US008663693B2

(12) United States Patent
Grenier et al.

(10) Patent No.: US 8,663,693 B2
(45) Date of Patent: Mar. 4, 2014

(54) NANOPARTICULATE FORMULATIONS OF FENOFIBRATE

(75) Inventors: Pascal Grenier, Kappelen (FR); Guy Vergnault, Kembs Loechle (FR); Alain Nhamias, Bartenheim (FR)

(73) Assignee: Jagotec AG, Muttenz (CH)

(*) Notice: Subject to any disclaimer, the term of this patent is extended or adjusted under 35 U.S.C. 154(b) by 1767 days.

(21) Appl. No.: 10/486,299

(22) PCT Filed: Aug. 9, 2002

(86) PCT No.: PCT/GB02/03687
§ 371 (c)(1),
(2), (4) Date: Dec. 17, 2004

(87) PCT Pub. No.: WO03/013474
PCT Pub. Date: Feb. 20, 2003

(65) Prior Publication Data
US 2005/0095297 A1 May 5, 2005

(30) Foreign Application Priority Data
Aug. 9, 2001 (GB) .................................. 0119480.2

(51) Int. Cl.
A61K 9/14 (2006.01)
A61K 31/355 (2006.01)
A61K 31/215 (2006.01)

(52) U.S. Cl.
USPC ............................ 424/489; 514/458; 514/571

(58) Field of Classification Search
USPC ......................... 424/489, 440; 514/458, 571
See application file for complete search history.

(56) References Cited

U.S. PATENT DOCUMENTS

| | | | |
|---|---|---|---|
| 4,895,726 A | 1/1990 | Curtet et al. | 424/456 |
| 5,091,188 A | 2/1992 | Haynes | |
| 5,145,684 A | 9/1992 | Liversidge et al. | |
| 5,880,148 A | 3/1999 | Edgar et al. | |
| 5,891,469 A | 4/1999 | Amselem | |
| 5,891,845 A | 4/1999 | Myers | |
| 5,919,776 A * | 7/1999 | Hagmann et al. | 514/159 |
| 6,028,054 A | 2/2000 | Benet et al. | |
| 6,074,670 A | 6/2000 | Stamm et al. | 424/489 |
| 6,096,338 A | 8/2000 | Lacy et al. | |
| 6,121,234 A | 9/2000 | Benet et al. | |
| 6,180,138 B1 | 1/2001 | Engh et al. | |
| 6,193,985 B1 | 2/2001 | Sonne | |
| 6,277,405 B1 | 8/2001 | Stamm et al. | 424/462 |
| 6,375,986 B1 | 4/2002 | Ryde et al. | 424/489 |
| 6,589,552 B2 | 7/2003 | Stamm et al. | 424/457 |
| 6,652,881 B2 | 11/2003 | Stamm et al. | 424/462 |
| 2008/0227763 A1 | 9/2008 | Lanquetin et al. | |

FOREIGN PATENT DOCUMENTS

| | | |
|---|---|---|
| EP | 0 330 532 | 1/1989 |
| WO | WO 96/14830 | 5/1996 |
| WO | WO 96/21439 | 7/1996 |
| WO | WO 98/30360 | 7/1998 |
| WO | WO 98/31360 | 7/1998 |
| WO | WO 98/31361 | 7/1998 |
| WO | WO 99/29300 * | 6/1999 |
| WO | WO 99/40904 | 8/1999 |
| WO | WO-9948477 A1 | 9/1999 |
| WO | WO 99/65469 | 12/1999 |
| WO | WO 00/16749 | 3/2000 |
| WO | WO 00/30615 | 6/2000 |
| WO | WO 00/30616 | 6/2000 |
| WO | WO 00/51572 | 9/2000 |
| WO | WO 00/76482 A1 | 12/2000 |
| WO | WO 01/03693 | 1/2001 |
| WO | WO 01/21154 | 3/2001 |
| WO | WO-0115688 A1 | 3/2001 |
| WO | WO 01/37381 | 5/2001 |
| WO | WO 01/49262 | 7/2001 |
| WO | WO 02/39983 | 5/2002 |

OTHER PUBLICATIONS http://www.eastman.com/Online_Publications/pci102/pci110211.htm, "Eastman Vitamin E TPGS NF-Properties and Applications".
D. Fercej Temeljotov, et al., "Solubilization and Dissolution Enhancement for Sparingly Soluble Fenofibrate", Acta Pharm. 46 (1996) pp. 131-136.
J. Shepherd, "The Fibrates in Clinical Practice: Focus on Micronised Fenofibrate", Atherosclerosis 110 (Suppl.) (1994), S55-S63.
J.P. Guichard et al., "A Comparison of the Bioavailability of Standard or Micronized Formulations of Fenofibrate", Current Therapeutic Research, vol. 54, No. 5, Nov. 1993, pp. 610-614.
M-T. Sheu, et al., "Dissolution Studies of Fenofibrate in the Ethanolic Medium", The Chinese Pharmaceutical Journal, vol. 45, No. 1(1993), pp. 43-51.
M-T. Sheu, et al., "Characterization and Dissolution of Fenofibrate Solid Dispersion Systems", International Journal of Pharmaceutics, 103 (1994) pp. 137-146.

* cited by examiner

*Primary Examiner* — Blessing M Fubara
(74) *Attorney, Agent, or Firm* — Mintz Levin Cohn Ferris Glovsky and Popeo, P.C.; Muriel Liberto, Esq.

(57) ABSTRACT

Nanoparticles and nanoparticle formulations or suspensions are provided which comprise a fibrate and vitamin E TPGS. The nanoparticles may have a mean diameter, measured by photon correlation spectroscopy, in the range of from about 100 nm to about 900 nm. Pharmaceutical formulations and uses of such compositions are also provided.

8 Claims, No Drawings

NANOPARTICULATE FORMULATIONS OF FENOFIBRATE

FIELD OF THE INVENTION

The present invention relates to nanoparticulate forms of the group of drug substances known as fibrates; to methods of preparing said nanoparticles, formulations containing said nanoparticles, and the use of said nanoparticulate drug substances. In particular the present invention relates to nanosuspensions comprising fenofibrate.

BACKGROUND OF THE INVENTION

The fibrates are a group of drugs which are known as hypolipidaemic agents. They include bezafibrate, ciprofibrate, fenofibrate and gemfibrizol. The fibrates have the beneficial effect of lowering cholesterol levels in the blood and hence reducing the risk of coronary heart disease (CHD). Epidemiological studies have confirmed that elevated cholesterol is one of the most important risk factors of coronary heart disease. It accelerates the development of atherosclerosis and enhances the adverse effects of other risk factors such as smoking, obesity, diabetes and hypertension. Reducing elevated cholesterol levels lowers the incidence of coronary death and non-fatal myocardial infarction. The lipoproteins which carry cholesterol are classified according to their density: very low density lipoproteins (VLDL); low density lipoproteins (LDL); and high density lipoproteins (HDL). About 70% of the plasma total cholesterol is carried in the LDL fraction and the major atherogenic potential appears to be mediated by this fraction. HDL is generally regarded as having a protective effect. Fibrates reduces plasma LDL, VLDL and total triglycerides and raise plasma HDL.

The fibrates are currently only available as solid dosage forms. Thus for example, fenofibrate is commercially available in micronised form, formulated as capsules (LIPANTIL MICRO™) or tablets (SUPRALIP™) which formulations are indicated for the treatment of types IIa, IIb, III, IV and V hyperlipidaemia resistant to diet; the tablets are also indicated for use in dyslipidaemia in diabetes.

Fibrates have extremely low solubility in water. Thus for example fenofibrate has a solubility in water of around 6 μg/ml. This can adversely affect absorption of the drug substance in vivo, leading to poor bioavailability. Consequently higher amounts of the drug substance are required to achieve the desired blood levels. The poor solubility of the fibrates also restricts the options available for formulating the drug substance.

Following oral administration, the absorption of drugs from the intestine is mainly dependent on their solubility in the intestinal fluids and their intestinal permeability. Poorly soluble drugs generally have low dissolution rates and exhibit only a small concentration gradient across the intestinal mucosa, which can result in low and unreliable levels of absorption. Drug substances which have low solubility also suffer from disadvantages in respect of other routes of administration, for example, by injection. Thus, it may only be possible to achieve very dilute solutions which do not provide the required dosage. In such circumstances it may be necessary to administer the drug as a continuous infusion rather than as a bolus injection. In some cases it may not be possible to achieve formulations suitable for parenteral administration at all.

Thus, because of its physicochemical characteristics, mainly its poor water solubility, fenofibrate has a low bioavailability and furthermore, a huge difference between bioavailability in fasted and in fed conditions can be observed. This difference is known as the 'food effect'. Many different approaches have been tried in order to overcome these problems.

EP A 0330532 describes the co-micronization of fenofibrate with a surfactant, preferably sodium lauryl sulfate, which composition is said to have improved bioavailability. A similar improvement in biavailability was reported in WO 96/21439, which describes formulations of fenofibrate consisting of a semi solid matrix based on "lauroyl macrogolglycerides" (Gelucire 44/14®) However neither of these approaches provides 100% bioavailability and the "food effect" behavior was not solved.

An alternative approach is described in U.S. Pat. No. 6,180,138 in which the fenofibrate is comicronized with an hydrophilic ingredient prior mixing with a surfactant. The product is finally spray dried to provide a powder useful for tablets or capsules formulations.

WO 98/31361 teaches how to obtain a granulate of fenofibrate combined with a hydrophilic polymer and a surfactant. This process requires large amount of diluent and thus is not compatible with high dosages.

Moreover, WO 00/16749 describes the preparation of fenofibrate granules using wet granulation combining water and water miscible solvent.

U.S. Pat. No. 5,880,148 describes compositions which comprise a micronised mixture of fenofibrate with a solid surfactant, preferably sodium lauryl sulphate, and a vitamin E substance selected from tocopherols and their esters with organic acids. The preferred vitamin E substance is said to be dl-alpha-tocopherol acetate.

Self emulsifying drug delivery systems (SEDDS) as described in WO 99/29300 represent another approach to formulating drugs with low bioavailability. Thus, WO 99/29300 describes compositions of fenofibrate in a carrier system comprising a hydrophobic component, eg a glyceride, a hydrophilic component eg a polyethylene glycol and a surfactant. Also described is a self-emulsifying preconcentrate which comprises an oil phase, eg a glyceride, a surfactant phase comprising at least one non-ionic surfactant and a hydrophilic component eg a PEG. The surfactant may be inter alia vitamin E TPGS. In these compositions the fenofibrate is solubilised in the oil phase. However, these systems require high concentrations of surfactant in order to dissolve the active substance in the oil in a sufficent amount and to obtain the self-formation of a fine emulsion or a microemulsion upon dilution in the gastric fluid. Most of the time the payload which can be achieved is limited and not compatible with high doses. Moreover, the addition of ethanol or propylene glycol to this oil-based formulation in order to help drug dissolution and overcome crystallisation problems makes this formulation incompatible with hard shell of soft gel capsule presentations.

WO 01/49262 describes pre-emulsion concentrates of fenofibrate comprising a lipophilic phase preferably containing an oil based on glycerol or propylene glycerol esters; an emulsifying system containing a lipophilic surfactant and a hydrophilic co-surfactant and further comprising vitamin E acetate to stabilize the pre-concentrate. In these compositions, the fenofibrate is solubilised in the oil phase. The formulations may additionally contain vitamin E TPGS as a surfactant. It is reported in WO 01/49262 that the use of vitamin E acetate aids drug dissolution and inhibition of crystallization and thus obviates the use, of ethanol or propylene glycol.

Vitamin E TPGS is known to form liquid crystals at concentrations above 20% and in U.S. Pat. No. 5,891,845 tablets are formulated using this compound in order to utilise the advantages of the high solubilization power of the liquid crystalline phase. These formulations contain at least 50% vitamin E TPGS, eg 80% and above.

More generally oils and vitamins E TPGS have been described several times in patents as bioavailability enhancer (U.S. Pat. No. 6,121,234; U.S. Pat. No. 6,028,054; U.S. Pat. No. 6,096,338) and in public presentations ("Vit E TPGS as an emulsifier and a bioenhancer for drugs and lipophilic compounds" Adams, M W $6^{th}$ international conference on Pharmaveutical Technology Paris Jun. 2-4, 1992.) According to Eastman brochure (www.Eastman.com/Online_Publications/efc226a/efc22611.htm) using vit E TPGS as a vitamin E supplement provides enhanced bioavailability of vitamin E in animals and humans.

Significant efforts have been directed to producing drug substances in the form of microparticles and nanoparticles. However, preparation of such small particles is not a trivial matter and can give rise to further difficulties both in relation to technical aspects of the process and in obtaining a satisfactory product. Thus for example there can be difficulties, especially on a manufacturing scale in obtaining a consistent and narrow particle size range. Furthermore, it is necessary to obtain stable products, e.g. nanosuspensions, but microparticles and nanoparticles have a tendency to aggregate and flocculate, which has adverse consequences for the stability of the product. A number of different approaches have been investigated for the preparation of microparticles and nanoparticles.

U.S. Pat. No. 5,091,188 describes a method for preparing injectable solutions of water-insoluble drugs, which comprises reducing the crystalline drug substance to dimensions in the range 50 nm to 10 µm, by sonication or other processes inducing high shear, in the presence of a phospholipid or other membrane-forming amphipathic lipid, whereby the drug microcrystals become coated with said lipid.

U.S. Pat. No. 5,145,684 describes particles of crystalline drug substance having a non-cross linked surface modifier adsorbed on the surface and an effective average particle size of less than about 400 nm. These particles are said to be prepared by milling in the presence of grinding media, using for example a ball mill, an attrition mill, a vibratory mill or a media mill.

International Patent Application WO 96/14830 (U.S. Pat. No. 5,858,410) describes a drug carrier which comprises particles of a pure active compound which is insoluble or only sparingly soluble in water, which has an average diameter of 10 nm to 1,000 nm and the proportion of particles larger than 5 µm in the total population is less than 0.1%. Preparation of the particles, with or preferably without surfactant, by means of cavitation (e.g. using a piston-gap homogenizer) or by shearing and impact forces (i.e. the jet stream principle) is also described.

WO 00/30616 describes particle size reduction of fenofibrate using high pressure homogenization down to mean particle size of 0.91 µm. The stabilization of the system is obtained by using phospholipids combined with ionic or non-ionic surfactants. This application also describes how to obtain freeze dried product able to regenerate the nanosuspension upon dilution in the appropriate solvent. WO 00/30615 decribes similar suspension formulations. Particles with a mean diameter around 900 nm are obtained; however only formulations combining at least one phospholipid with another surfactant are stable. Fenofibrate suspensions stabilized using only phospholipids are reported as not stable.

Another approach of fenofibrate fine particle design is described in WO 99/65469 where supercritical fluid technology allows the manufacturing of particles having a mean diameter of 200 nm. Once again, the particle manufacturing requires the use of a mixture of phospholipids and ionic or non ionic surfactants. The limited solubility of fenofibrate in supercritical fluid could be an hurdle for high doses requirements because of the quantities of liquefied gaz which will be necessary to process.

International application WO 00/51572 describes the use of PEG-derivatized lipids as surface stabilizers for nanoparticulate compositions of poorly soluble drugs. The PEG-derivatised lipid may be a PEG-phospholipid, PEG-cholesterol, PEG-cholesterol derivative, PEG-vitamin A, PEG-vitamin E, or a mixture thereof. It is stated that the invention can be practiced with a wide variety of drugs, and various classes of drugs are listed; there is no specific reference to hypolipidaemic agents. However, it appears from the only example using PEG vit E derivative that this compound does not provide the expected result. As stated in the conclusion of this example, "none of the tested surfactants (in vit E PEG) resulted in a stable non agglomerated nanoparticulate composition."

DESCRIPTION OF THE INVENTION

We have now surprisingly found that fibrates, e.g. fenofibrate, can advantageously be prepared as a stable nanosuspension without phospholipid stabilisers, by using vitamin E TPGS (tocopherolpolyethyleneglycolsuccinate) as stabiliser. We have further found that said nanosuspension comprises nanoparticles which have a consistent and narrow particle size range. In addition, the nanosuspension has improved bioavailability.

In a first aspect therefore the present invention provides nanoparticles comprising a fibrate and vitamin E TPGS, said nanoparticles having a mean diameter, measured by photon correlation spectroscopy, in the range of from about 100 nm to about 900 nm, preferably 400 nm to 600 nm. Said nanoparticles are preferably provided as a nanosuspension, preferably an aqueous nanosuspension.

The fibrate may be selected from any of the known fibrate drugs, in particular bezafibrate, ciprofibrate, fenofibrate and gemfibrizol. The fibrate is preferably fenofibrate.

The ratio of fenofibrate:vitamin E TPGS (by weight) in the formulations is from 40:0.1 to 1:10 most preferably 20:1.

As is well known in the pharmaceutical art, particle size may be measured by a variety of methods, which can give rise to apparently different reported particle sizes. Such methods include photon correlation spectroscopy (PCS) and laser diffraction. Furthermore the particle size may be reported as an average particle size (e.g. a number average, weight average or volume average particle size). In the present specification, unless indicated otherwise, the particle size will be quoted as a volume average particle size. Thus for example, a $D_{50}$ of 500 nm indicates that 50% by volume of the particles have a diameter of less than 500 nm. Alternatively it can be stated that the particles having a diameter of less than 500 nm occupy 50% of the total volume occupied by the total number of particles.

When the particle size of fenofibrate according to the present invention is measured by laser diffraction the $D_{50}$ is in the range 350-750 nm and the $D_{99}$ is in the range 500-900 nm.

It will be appreciated that the vitamin E TPGS incorporated in the formulations according to the present invention will function both as a surface stabiliser and to enhance the bioavailability of the fibrate. However, nanosuspensions and nanoparticles comprising a fibrate according to the present invention may, if desired, include a further stabiliser (other than a phospholipid) to prevent aggregation of the nanoparticles. Such stabilisers, which are well known in the art, are described in more detail hereinafter.

In this specification nanoparticles comprising and nanosuspensions comprising a fibrate, eg fenofibrate, and vitamin E TPGS according to the present invention will be referred to as nanoparticulate fibrate. It should be appreciated that this term also includes such formulations which also comprise a further stabiliser.

Additional stabilisers which may be employed in the preparation of nanosuspensions according to the present invention may be selected from conventional stabilisers, and may include compounds which are also described as surfactants and surface modifiers. Thus examples of stabiliser which may be employed include:

polyoxyethylene sorbitan fatty acid esters, e.g. Tweens and Spans; polyoxyethylene stearates; polyoxyethylene alkyl esters; polyethylene glycols; block polymers and block copolymers such as poloxamers e.g Lutrol F68, and poloxamines; sterols (e.g. cholesterin derivatives, as well as stigmasterin), esters and ethers of sugars or sugar alcohols with fatty acids or fatty alcohols (e.g. saccharose monostearate);

ethoxylated mono- and diglycerides, ethoxylated lipids and lipoids, dicetyl phosphate, sodium cholate, sodium glycolcholate, sodium taurocholate; sodium citrate;

cellulose ethers and cellulose esters (e.g. methyl cellulose, hydroxyethyl cellulose, hydroxypropyl cellulose, sodium carboxymethyl cellulose), polyvinyl derivatives such as polyvinyl alcohol, polyvinyl pyrrolidone, polyvinyl acetate, alginates, polyacrylates (e.g. carbopol), xanthanes; pectins, gelatin, casein, gum acacia, cholesterol, tragacanth, stearic acid, calcium stearate, glyceryl monostearate, dioctyl sodium sulfosuccinate (sodium docusate); sodium lauryl sulfate, sodium dodecyl sulphate, benzalkonium chloride, alkyl aryl polyether sulfonate, polyethylene glycols;

colloidal silicon dioxide, magnesium aluminium silicate; and phosphates.

Preferably, the formulations are prepared with vitamin E TPGS and without an additional stabiliser.

Nanoparticulate fibrates, e.g. nanoparticulate fenofibrate according to the invention, may be prepared by any known method for the preparation of nanoparticles, in particular by cavitation.

In a second aspect the present invention provides a process for preparing nanoparticles comprising a fibrate, e.g. fenofibrate which comprises subjecting a coarse dispersion of said fibrate to cavitation. Preferably the nanoparticles are prepared using a high pressure piston-gap homogeniser.

For the preparation of nanoparticles it is preferred that the fibrate starting material be utilised in the form of coarse particles, preferably having a particle size of less than about 100 µm. If necessary, the particle size of the fibrate may be reduced to this level by conventional means, such as milling. The coarse particles of fibrate are preferably dispersed in a liquid medium comprising a solvent in which the drug substance is essentially insoluble. In the case of fibrates the liquid medium preferably comprises an aqueous solvent and most preferably consists essentially of water. The concentration of fibrate in the said dispersion of coarse particles may be in the range 0.1 to 50%. The coarse dispersion may then be utilised in any known method for obtaining nanoparticles.

A preferred method is high pressure homogenization, wherein particle size is reduced mainly by cavitation. This is most preferably achieved using a high pressure piston-gap homogeniser. In this method, the dispersion of coarse particles is forced at a high flow rate through a gap which is approximately 25 µm wide. The static pressure exerted on the liquid falls below the vapour pressure of the liquid. The liquid therefore boils, resulting in the formation of gas bubbles within the area of the gap. However, once the liquid exits from the gap, normal pressure prevails and the gas bubbles collapse. The powerful implosion forces which result are strong enough to break up the coarse particles of drug substance, resulting in the formation of nanoparticles.

High pressure homogenisation may be carried out at a pressure in the range 100 to 3000 bar, preferably 1000 to 2000 bar ($10^7$ to $3\times10^8$ Pa, preferably $10^8$ to $2\times10^8$ Pa) and at a temperature in the range 0 to 50° C., preferably 10 to 20° C., eg around 15° C. The homogenisation may be carried out in a series of cycles until the desired particle size is obtained, or as a continuous process, e.g. over a period of 2-30 hours, preferably 2-10 hours, e.g. 4 hours.

The vitamin E TPGS and/or an additional stabiliser (if employed) may be introduced at any suitable stage during the manufacture of the nanosuspension. Thus for example, vitamin E TPGS may be added to the initial coarse dispersion prior to the formation of nanoparticles or after reduction of the particles size, e.g. by high pressure homogenization, has taken place. Alternatively a portion of the vitamin E TPGS may be added before and a portion after the step of particle size reduction. Preferably vitamin E TPGS is present in the coarse dispersion.

When an additional stabiliser is employed, the concentration of said stabiliser, either in the coarse dispersion or the nanosuspension may be in the range 0 to 10%.

It will be appreciated from the foregoing that the process is carried out in a liquid medium and hence the nanoparticulate fibrate product is initially obtained in the form of a nanosuspension. If desired the liquid medium may be removed, e.g. by lyophilisation or spray drying to provide nanoparticulate fibrate in solid form. It will be appreciated that where a stabiliser is present during the manufacture of a nanosuspension, the corresponding dried nanoparticulate product will be associated with said stabiliser.

The fibrate nanosuspensions according to the invention may optionally be admixed with a nanoemulsion, comprising a lipid together with a stabiliser. The lipid may be for example a fatty acid glyceride, such as a vegetable oil, eg peanut oil, coconut oil, palm oil, olive oil, corn oil and the like.

The stabiliser may be a conventional stabiliser, such as those listed above, eg a Span or Tween.

The nanoemulsion may be prepared by mixing a lipid and stabiliser (lipidic phase) with an aqueous phase (eg water). The mixture may be initially subjected to dispersion, using a high shear dispersion instrument, to form an emulsion. A nanoemulsion may then be prepared by subjecting the emulsion to cavitation, eg using a piston-gap homogeniser, in a similar manner to that described above for nanoparticles of the drug substance. The nanosuspension and nanoemulsion may then be mixed according to conventional techniques, eg simple stirring.

Following admixture of the nanosuspension and nanoemulsion, a portion of the fibrate active ingredient may become solubilised in the oil phase. Alternatively the fibrate may be incorporated into the lipidic phase of a nanoemulsion prior to admixture of the nanosuspension and nanoemulsion, to increase the payload of the composition. One portion of the drug is present in a dissolved form in the oil droplets and another portion is undissolved and finely dispersed as stabilized nanoparticles in the nanosuspension.

The fibrate nanosuspensions and nanoparticles according to the present invention may be formulated for pharmaceutical use, optionally using pharmaceutically acceptable excipients and carriers well known in the art. They may be administered as a medicament by any convenient route, eg by parenteral, oral, topical, buccal, sublingual, nasal, pulmonary, rectal or transdermal administration.

In a third aspect therefore the invention provides a pharmaceutical formulation comprising nanoparticles comprising a fibrate, e.g. fenofibrate said nanoparticles having a mean diameter, measured by photon correlation spectroscopy, in the range of from about 100 nm to about 900 nm, preferably 400 nm to 600 nm. Pharmaceutical formulations according to the present invention advantageously comprise a nanosuspension, most preferably in aqueous solution. Pharmaceutical formulations according to the present invention may be prepared according to methods well known in the art.

Thus for example, solid dosage forms, eg for oral administration may be prepared by spray-coating the nanosuspension comprising a fibrate such as fenofibrate on to a sugar sphere or other suitable solid pharmaceutical excipient.

Dosage forms for pulmonary administration by inhalation may be provided as an aerosol, comprising an aqueous nanosuspension of a fibrate e.g. fenofibrate.

A dry powder for inhalation may be prepared by spraying the aqueous dispersion on to carrier particles, such as lactose.

Fibrate formulations according to the present invention may be used for reducing plasma cholesterol levels, therefore reducing the risk of coronary heart disease and other conditions which may be treated with a hypolipidaemic agent. Reducing plasma cholesterol levels also reduces the adverse effects of smoking, obesity, diabetes and hypertension, thereby lowering the incidence of coronary death and non-fatal myocardial infarction.

In a fourth aspect of the invention, there is provided a nanoparticulate fibrate as defined in accordance with the first aspect of the invention for use in medicine.

In a fifth aspect the present invention provides the use of a nanoparticulate fibrate as defined in accordance with the first aspect e.g. nanoparticulate fenofibrate in the treatment of a condition known to be treatable with a hypolipidaemic agent, eg reduction of blood cholesterol levels. Such uses include, the use of a nanoparticulate fenofibrate as defined in accordance with the first aspect of the invention in the preparation of a medicament for the treatment of atherosclerosis, obesity, myocardial infarction, diabetes or hypertension.

This aspect also extends to methods of treatment of conditions known to be treatable with a hypolipidaemic agent, such as hyperlipidaemia, for example treatment of atherosclerosis, obesity, myocardial infarction, diabetes or hypertension, the method comprising administering to a subject in need thereof a therapeutic amount of a pharmaceutical formulation of a nanoparticulate fenofibrate as defined above.

Preferred features for the second and subsequent aspects of the invention are as for the first mutatis mutandis.

EXPERIMENTAL

Table I illustrates representative preparations of fenofibrate according to the present invention.

Example 1

Preparation of the Nanosuspensions with Vitamin E TPGS.
A) Preparation of the Slurry: 100 g
  Fenofibrate: 10.00 g
  Vitamin E TPGS: 0.50 g
  Water for injection: 89.50 g A preparation of an aqueous solution of stabilizer (Vit E TPGS) was incorporated into water for injection under magnetic stirring (IKA 500 rpm at 50° C.) until a clear solution was obtained. A slurry was formed by wetting fenofibrate with the appropriate quantity of the aqueous solution of the surfactant. The resulting suspension was dispersed using a high shear dispersing instrument (Polytron PT, 11 000 rpm for 1 min). The particle diameter (in microns, volume %) measured by laser diffractometry (Coulter LS 230) provided the following results: 3 runs were made.

|     | Run 1 | Run 2 | Run 3 |
|-----|-------|-------|-------|
| d10 | 0.577 | 0.579 | 0.583 |
| d50 | 6.787 | 6.776 | 6.765 |
| d90 | 16.12 | 16.03 | 15.94 |
| d95 | 18.69 | 18.58 | 18.49 |
| d99 | 23.03 | 22.73 | 22.63 |

B) Preparation of the Nanosuspension: 100 g

The resulting suspension from Ex 1(A) was passed through a high pressure piston gap homogenizer to obtain a nanosuspension. This was prepared using an Avestin C50: the homogenizing pressure was set at 1500 bars for 240 min using a "sharp edge" design valve having a 11.34 mm length. During homogenization the drug particles are disrupted due to cavitation effects and shear forces to form nanoparticles. The particle diameter (in microns, volume %) measured by laser diffractometry (Coulter LS 230) provided the following results (3 runs were made)
  Run1-Run 2-Run 3
  d10: 0.362-0.366-0.366
  d50: 0.448-0.459-0.458
  d90: 0.540-0.557-0.549
  d95: 0.557-0.556-0.556
  d99: 0.596-0.630-0.612

The particle size (hydrodynamic mean diameter) was also measured by PCS (Photon Correlation Spectroscopy) using a Zetasizer 300 HS (Malvern); 4 analysis were made and provided the following results: 409 nm-405 nm-407 nm-407 nm.

This nanosuspension was demonstrated to be physically stable after 2 months of storage at 4° C. (it is considered that a dispersed system is stable when the relative standard deviation (RSD) is lower or equal to 10% of the nominal value obtained at t0).

The particle diameter (in microns, volume %) measured by laser diffractometry (Coulter LS 230) provided the following results (3 runs were made)
  Run1-Run 2-Run 3
  d10: 0.349-0.349-0.349
  d50: 0.435-0.436-0.436
  d90: 0.529-0.530-0.530
  d95: 0.549-0.550-0.550
  d99: 0.591-0.592-0.592

The particle size (hydrodynamic mean diameter) was also measured by PCS (Photon Correlation Spectroscopy) using a Zetasizer 3000 HS (Malvern); 4 runs were made and provided the following results: 432 nm-429 nm-429 nm.

Example 2

Mixing of a Nanoemulsion and a Nanosuspension
A) Preparation of the Slurry: 100 g
  Fenofibrate: 10.00 g
  Vitamin E TPGS: 0.50 g
  Water for injection: 89.50 g A preparation of an aqueous solution of stabilizer (Vit E TPGS) was incorporated into water for injection under magnetic stirring (IKA 500 rpm at 50° C.) until a clear solution was obtained. A slurry was formed by wetting fenofibrate with the appropriate quantity of the aqueous solution of the surfactant. The resulting suspension was dispersed using a high shear dispersing instrument (Polytron PT, 11 000 rpm for 1 min). The measurement of the particle diameter (in microns, volume %) by laser diffractometry (Coulter LS 230) was not carried out.

B) Preparation of the Nanosuspension: 100 g

The resulting suspension from Ex 2(A) was passed through a high pressure piston gap homogenizer to obtain a nanosuspension. This was prepared using an Avestin C50: the homogenizing pressure was set at 1500 bars for 240 min using a "sharp edge" design valve having a 11.34 mm length. During homogenization the drug particles are disrupted due to cavitation effects and shear forces to form nanoparticles. The particle diameter (in microns, volume %) measured by laser diffractometry (Coulter LS 230) provided the following results (3 runs were made)

Run1-Run 2-Run 3
d10: 0.406-0.418-0.418
d50: 0.510-0.520-0.519
d90: 0.631-0.636-0.636
d95: 0.655-0.659-0.658
d99: 0.711-0.712-0.712

The particle size (hydrodynamic mean diameter) was also measured by PCS (Photon Correlation Spectroscopy) using a Zetasizer 300 HS (Malvern); 4 analysis were made and provided the following results: 480 nm-477 nm-474 nm-486 nm.

C) Preparation of the Emulsion: 40 g

Peanut oil: 4.00 g
Span 20: 0.80 g
Water for injection: 35.20 g

Water for injection pre-heated to 50° C. was added to the lipidic phase containing peanut oil and Span 20 which were also pre-heated up to 50° C. Then the emulsion was dispersed using a high shear dispersing instrument (Polytron PT 3100). The particle diameter (in microns, volume %) measured by laser diffractometry (Coulter LS 230) provided the following results (3 runs were made)

Run1-Run 2-Run 3
d10: 0.905-0.864-0.855
d50: 5.549-5.499-5.485
d90: 15.89-16.21-16.28
d95: 18.25-18.59-18.64
d99: 21.34-21.83-21.88

D). Preparation of the Nanoemulsion: 40 g

The resulting emulsion from Ex 2(C) was passed through a high pressure piston gap homogenizer to obtain a nanoemulsion. The formulation was prepared using an Avestin C50: the homogenizing pressure was set at 500 bars for 30 min using a "sharp edge" design valve having a 11.34 mm length. During homogenization the lipidic droplets are disrupted due to cavitation effects and shear forces to form solid lipidic nanoparticles. The particle diameter (in microns, volume %) measured by laser diffractometry (Coulter LS 230) provided the following results (3 runs were made)

Run1-Run 2-Run 3
d10: 0.090-0.087-0.089
d50: 0.279-0.282-0.283
d90: 0.435-0.436-0.437
d95: 0.473-0.474-0.475
d99: 0.538-0.538-0.539

The particle size (hydrodynamic mean diameter) was also measured by PCS (Photon Correlation Spectroscopy) using a Zetasizer 300 HS (Malvern); 4 analysis were made and provided the following results: 245 nm-245 nm-243 nm-243 nm.

E) Mixing of the Nanosuspension and Nanoemulsion to Form a Colloïdal Dispersion

Mixing of the nanosuspension from Ex 2 (B) (10.0 g) and the nanoemulsion from Ex 2 (D) (0.5 g) was made under magnetic stirring (500 rpm for 5 min).

The particle diameter (in microns, volume %) measured by laser diffractometry (Coulter LS 230) provided the following results (3 runs were made)

Run1-Run 2-Run 3
d10: 0.433-0.435-0.435
d50: 0.562-0.562-0.561
d90: 0.713-0.711-0.710
d95: 0.757-0.754-0.754
d99: 0.828-0.823-0.822

The particle size (hydrodynamic mean diameter) was also measured by PCS (Photon Correlation Spectroscopy) using a Zetasizer 300 HS (Malvern); 4 analysis were made and provided the following results: 511 nm-516 nm-511 nm-520 nm.

This nanosuspension was demonstrated to be physically stable after 2 months of storage at 4° C. (it is considered that a dispersed system is stable when the relative standard deviation (RSD) is lower or equal to 10% of the nominal value obtained at t0).

The particle diameter (in microns, volume %) measured by laser diffractometry (Coulter LS 230) provided the following results (3 runs were made)

Run1-Run 2-Run 3
d10: 0.456-0.458-0.459
d50: 0.592-0.593-0.594
d90: 0.762-0.761-0.760
d95: 0.804-0.802-0.798
d99: 0.870-0.868-0.866

The particle size (hydrodynamic mean diameter) was also measured by PCS (Photon Correlation Spectroscopy) using a Zetasizer 3000 HS (Malvern); 3 runs were made and provided the following results: 498 nm-486 nm-482 nm.

Example 3

Mixing of a Nanoemulsion and a Nanosuspension

A) Preparation of the Emulsion: 40 g

Peanut oil: 4.00 g
Span 20: 0.80 g
Fenofibrate: 0.20 g
Water for injection: 35.20 g Fenofibrate, peanut oil and Span 20 were pre-heated up to 50° C. and mixed together under magnetic sting in the mean time until a clear lipidic phase is obtained.

Water for injection pre-heated to 50° C. was added to the lipidic phase containing peanut oil, fenofibrate and Span 20 which were also pre-heated up to 50° C.

Then the emulsion was dispersed using a high shear dispersing instrument (Polytron PT 3100). The particle diameter (in microns, volume %) measured by laser diffractometry (Coulter LS 230) provided the following results (3 runs were made)

Run1-Run 2-Run 3
d10: 0.868-0.883-0.910
d50: 4.913-4.822-4.728
d90: 10.92-10.84-10.62
d95: 11.74-11.69-11.45
d99: 12.95-12.91-12.63

B). Preparation of the Nanoemulsion: 40 g

The resulting emulsion from Ex 3(A) was passed through a high pressure piston gap homogenizer to obtain a nanoemulsion. The formulation was prepared using an Avestin C5: the homogenizing pressure was set at 500 bars for 30 min using a "sharp edge" design valve having a 11.34 mm length. During homogenization the lipidic droplets are disrupted due to cavitation effects and shear forces to form solid lipidic nanoparticles. The particle diameter (in microns, volume %) measured by laser diffractometry (Coulter LS 230) provided the following results (3 runs were made)

Run1-Run 2-Run 3
d10: 0.083-0.084-0.082
d50: 0.286-0.287-0.285
d90: 0.459-0.460-0.457
d95: 0.500-0.501-0.498
d99: 0.578-0.579-0.577

The particle size (hydrodynamic mean diameter) was also measured by PCS (Photon Correlation Spectroscopy) using a Zetasizer 3000 HS (Malvern); 4 analysis were made and provided the following results: 246 nm-249 nm-253 nm. Particle size obtained with drug loaded nanoemulsion are quite similar to those obtained of the "placebo" one described in Example 2

This active loaded nanoemulsion is then mixed with a drug loaded nanosuspension following procedure described in Example 2 step E to form a final formulation containing one part of the active dissolved in oil nanodroplets and one part dispersed as nanoparticles.

Example 4

Freeze Dried Fenofibrate Nanosuspension

A fenofibrate nanosuspension was freeze dried with 5% w/w of trehalose as a "carrier"

1. Preparation of the Slurry: 150 g
Fenofibrate: 10.00 g
Vitamin E TPGS: 0.50 g
Water for injection: 89.50 g A preparation of an aqueous solution of stabilizer (Vit E TPGS) was incorporated into water for injection under magnetic stirring (IKA 500 rpm at 50° C.) until a clear solution was obtained. A slurry was formed by wetting fenofibrate with the appropriate quantity of the aqueous solution of the surfactant. The resulting suspension was dispersed using a high shear dispersing instrument (Polytron PT, 11 000 rpm for 1 min). The measurement of the particle diameter (in microns, volume %) by laser diffractometry (Coulter LS 230) provided the following results: 3 runs were made.

Run1-Run 2-Run 3
d10: 0.608-0.601-0.600
d50: 7.001-6.927-6.899
d90: 16.48-16.25-16.14
d95: 19.00-18.72-18.61
d99: 23.43-22.86-22.70

2. Preparation of the Nanosuspension: 150 g

The resulting suspension was passed through a high pressure piston gap homogenizer to obtain a nanosuspension. Formulation 9420-050/13AN was prepared using an Avestin C50: the homogenizing pressure was set at 1500 bars for 300 min using a "sharp edge" design valve having a 11.34 mm length. During homogenization the drug particles are disrupted due to cavitation effects and shear forces to form nanoparticles. The particle diameter (in microns, volume %) measured by laser diffractometry (Coulter LS 230) provided the following results (3 runs were made)

Run1-Run 2-Run 3
d10: 0.412-0.414-0.413
d50: 0.514-0.516-0.516
d90: 0.632-0.633-0.634
d95: 0.655-0.655-0.656
d99: 0.710-0.711-0.712

The particle size (hydrodynamic mean diameter) was also measured by PCS (Photon Correlation Spectroscopy) using a Zetasizer 3000 HS (Malvern); 3 runs were made and provided the following results: 477 nm-481 nm-481 nm.

3. Preparation of the Freeze Dried Nanoparticles: 150 g (9420-050/07FD)

7.5 g of trehalose are added under gentle stirring the the fenofibrate nanosuspension Six samples of 2 ml each of the trehalose/fenofibrate nanosuspension were submitted to freeze drying. The freeze drying process parameters were set up at:

Pre freezing temperature: −35° C.
Drying temperature: +5° C.
Pression: 0.940 mbar
Processing time: freezing=1 h 30 min–drying=18 h 30 min The particle diameter (in microns, volume %) measured by laser diffractometry (Coulter LS 230) provided the following results (3 runs were made)

Run1-Run 2-Run 3
d10: 0.403-0.408-0.414
d50: 0.551-0.556-0.563
d90: 0.741-0.745-0.751
d95: 0.789-0.790-0.797
d99: 0.870-0.872-0.882

The particle size (hydrodynamic mean diameter) was also measured by PCS (Photon Correlation Spectroscopy) using a Zetasizer 3000 HS (Malvern); 3 runs were made and provided the following results: 619 nm-626.7 nm-637 nm to be compared with 477 nm-481 nm and 481 nm obtained before freeze drying

The invention claimed is:

1. Stable nanoparticles comprising a fibrate and vitamin E TPGS without an additional stabilizer, said nanoparticles having a mean diameter, measured by photon correlation spectroscopy, in the range of from about 100 nm to about 900 nm.

2. A stable nanoparticulate fibrate formulation of fenofibrate, vitamin E TPGS and water compatible with a hard shell or soft shell capsule, wherein the nanoparticulate fibrate is in the form of an aqueous nanosuspension without additional stabilizer.

3. A method for treatment of hyperlipidaemia, comprising administering to a subject in need thereof a therapeutic amount of a pharmaceutical formulation of a nanoparticle fibrate according to claim 1 or claim 2.

4. Nanoparticles according to claim 1 wherein the fibrate is fenofibrate.

5. A pharmaceutical formulation comprising the nanoparticles of claim 1.

6. Nanoparticles according to claim 1, wherein said nanoparticle is stable for two months at 4° C.

7. A pharmaceutical formulation comprising the nanoparticulate fibrate of claim 2.

8. A nanoparticulate fibrate formulation according to claim 2, wherein said wherein said formulation is stable for two months at 4° C.

* * * * *

UNITED STATES PATENT AND TRADEMARK OFFICE
CERTIFICATE OF CORRECTION

PATENT NO. : 8,663,693 B2  
APPLICATION NO. : 10/486299  
DATED : March 4, 2014  
INVENTOR(S) : Pascal Grenier et al.

Page 1 of 1

It is certified that error appears in the above-identified patent and that said Letters Patent is hereby corrected as shown below:

In the Claims

Column 12, line number 61, claim 8, delete the first instance of the words "wherein said".

Signed and Sealed this
Twenty-fourth Day of June, 2014

Michelle K. Lee
*Deputy Director of the United States Patent and Trademark Office*